United States Patent
Watanabe et al.

(10) Patent No.: US 9,723,994 B2
(45) Date of Patent: Aug. 8, 2017

(54) OBJECT INFORMATION ACQUISITION APPARATUS, OBJECT INFORMATION ACQUISITION SYSTEM, DISPLAY CONTROL METHOD, DISPLAY METHOD, AND PROGRAM

(75) Inventors: Tadaki Watanabe, Tokyo (JP); Koichiro Wanda, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 808 days.

(21) Appl. No.: 13/567,961

(22) Filed: Aug. 6, 2012

(65) Prior Publication Data

US 2013/0044563 A1 Feb. 21, 2013

(30) Foreign Application Priority Data

Aug. 8, 2011 (JP) ................................ 2011-172975
Jul. 12, 2012 (JP) ................................ 2012-156630

(51) Int. Cl.
*G03B 42/06* (2006.01)
*A61B 5/00* (2006.01)

(52) U.S. Cl.
CPC ............ *A61B 5/0095* (2013.01); *A61B 5/748* (2013.01); *A61B 5/0077* (2013.01); *A61B 5/7203* (2013.01)

(58) Field of Classification Search
CPC ........ G03B 42/06; A61B 5/748; A61B 5/0095
USPC ........................................................... 367/7
See application file for complete search history.

(56) References Cited

U.S. PATENT DOCUMENTS

| | | | | |
|---|---|---|---|---|
| 2,513,282 A | * | 7/1950 | Busignies | 342/58 |
| 2,759,783 A | * | 8/1956 | Ross | 346/8 |
| 2,922,837 A | * | 1/1960 | Boothroyd et al. | 348/260 |
| 3,135,955 A | * | 6/1964 | Brainin et al. | 244/177 |
| 4,975,968 A | * | 12/1990 | Yukl | G01N 22/00 324/647 |
| 5,157,518 A | * | 10/1992 | Ohtaki et al. | 358/461 |
| 7,068,867 B2 | * | 6/2006 | Adoram | A61B 8/0833 385/12 |
| 8,223,143 B2 | * | 7/2012 | Dastmalchi | A61B 3/102 345/418 |
| 9,339,254 B2 | * | 5/2016 | Wanda | A61B 5/14542 |
| 2002/0015196 A1 | * | 2/2002 | Kitamura et al. | 358/505 |
| 2004/0131299 A1 | * | 7/2004 | Adoram | A61B 8/0833 385/12 |
| 2004/0223022 A1 | * | 11/2004 | Endo | 347/19 |

(Continued)

FOREIGN PATENT DOCUMENTS

JP 2010022812 A 2/2010

*Primary Examiner* — Luke Ratcliffe
*Assistant Examiner* — Amie M N'Dure
(74) *Attorney, Agent, or Firm* — Canon USA Inc., IP Division

(57) ABSTRACT

An object information acquisition apparatus, configured to receive an acoustic wave from an object and acquire characteristic information of the object, includes a receiver configured to receive the acoustic wave and convert the received acoustic wave into an electric signal, a scan control unit configured to scan the receiver at least in one direction, and a display control unit configured to produce guide information for displaying a guide on a display unit, wherein the guide is in terms of the number of times the receiver is scanned in a first direction and wherein the guide information is produced using information associated with a specified region defined by a user as a region in which characteristic information is to be acquired.

17 Claims, 9 Drawing Sheets

(56) References Cited

U.S. PATENT DOCUMENTS

| | | | | |
|---|---|---|---|---|
| 2004/0257601 | A1* | 12/2004 | Tomiyasu et al. | 358/1.9 |
| 2004/0267135 | A1* | 12/2004 | Takeuchi | 600/459 |
| 2005/0024393 | A1* | 2/2005 | Kondo et al. | 347/2 |
| 2007/0016035 | A1* | 1/2007 | Hashimoto | A61B 8/0833 600/437 |
| 2007/0044364 | A1* | 3/2007 | Sammut | F41G 1/473 42/122 |
| 2007/0153325 | A1* | 7/2007 | Mizumukai | 358/1.15 |
| 2008/0030680 | A1* | 2/2008 | Tsukada et al. | 351/206 |
| 2008/0045804 | A1* | 2/2008 | Williams | 600/300 |
| 2009/0054776 | A1* | 2/2009 | Sasaki | 600/443 |
| 2009/0131793 | A1* | 5/2009 | Stonefield | A61B 8/00 600/443 |
| 2010/0053618 | A1* | 3/2010 | Nakajima et al. | 356/432 |
| 2010/0076612 | A1* | 3/2010 | Robertson | 700/286 |
| 2010/0104167 | A1* | 4/2010 | Sakaguchi et al. | 382/132 |
| 2010/0152623 | A1* | 6/2010 | Williams | 600/595 |
| 2010/0278008 | A1* | 11/2010 | Ammar | 367/7 |
| 2011/0208057 | A1* | 8/2011 | Oikawa | A61B 5/0095 600/443 |
| 2012/0075652 | A1* | 3/2012 | Miyamoto | 358/1.13 |
| 2013/0245460 | A1* | 9/2013 | King | A61B 5/0077 600/476 |

* cited by examiner

OBJECT INFORMATION ACQUISITION APPARATUS, OBJECT INFORMATION ACQUISITION SYSTEM, DISPLAY CONTROL METHOD, DISPLAY METHOD, AND PROGRAM

BACKGROUND OF THE INVENTION

1. Field of the Invention

The present invention relates to an object information acquisition apparatus for use in medical diagnosis, nondestructive inspection, or the like, an object information acquisition system, a display control method, a display method, and a program.

2. Description of the Related Art

A photo acoustic imaging (PAI) technique is known as one of photo imaging techniques using light. In the PAI technique, a living body given as an object is illuminated with light. An acoustic wave is generated when photo energy is absorbed by a part such as a tumor in the object, and the generated acoustic wave is received by a receiver. A reception signal output from the receiver is analyzed and optical characteristic information of the inside of the living body is acquired as image data.

Japanese Patent Laid-Open No. 2010-022812 discloses an apparatus configured such that a breast is held from both sides thereof with a holding unit, and a receiver is two-dimensionally scanned over the holding unit while receiving an acoustic wave. By two-dimensionally scanning the receiver, it is possible to obtain characteristic information at a plurality of positions in the object.

SUMMARY OF THE INVENTION

In a case where the receiver is two-dimensionally scanned in a main scanning direction and a sub scanning direction as with the technique disclosed in Japanese Patent Laid-Open No. 2010-022812, scanning may be performed not over a whole scannable region but only within a particular region specified by a user or an operator to acquire characteristic information of this region in the object. More specifically, an image of the object held with the holding unit may be taken by a camera, and the image thereof may be displayed on a display screen such that a user or an operator is allowed to specify a particular region on the display screen.

However, a reception time period needed to receive an acoustic wave for acquiring characteristic information of the specified region (the time period necessary to receive the acoustic wave at all scanning positions) does not necessarily change in proportion of the size of the specified region. In particular, when the receiver is scanned at a low speed, the reception time period varies greatly depending on the number of times the main scanning and the sub scanning are performed to acquire characteristic information of the specified region. However, in known techniques, when a user defines a specified region to be scanned to acquire characteristic information, no information is provided to the user in terms of the number of times the receiver is scanned.

Therefore, a slight difference in the specified region may result in an unnecessary increase in the number of scans performed by the receiver in the main or sub scanning direction, which may create a redundant time period in the acoustic wave reception time period for acquiring characteristic information, which may in turn redundantly increase a time period during which a person under examination is constrained.

In view of the above, the present invention provides a technique that allows a user to recognize at least the number of times a receiver is scanned in one direction when the user defines a specified region to be scanned to acquire characteristic information.

According to an aspect of the present invention, an object information acquisition apparatus, configured to receive an acoustic wave from an object and acquire characteristic information of the object, includes a receiver configured to receive the acoustic wave and convert the received acoustic wave into an electric signal, a scan control unit configured to scan the receiver at least in one direction, and a display control unit configured to produce, using information associated with a specified region defined by a user as a region in which characteristic information is to be acquired, guide information for displaying a guide on a display unit in terms of the number of times the receiver is scanned in a first direction.

According to an aspect of the present invention, a display control method includes receiving information associated with a specified region defined by a user as a region in which characteristic information of an object is to be acquired, and producing guide information for displaying, on a display unit, a guide at least in terms of the number of times a receiver is scanned in a first direction, the receiver being configured to receive an acoustic wave from the object to acquire the characteristic information, the guide information being produced using information associated with the specified region. According to an aspect of the invention, a display method includes displaying a captured image of the object, and displaying a guide in terms of a specified region defined by a user as a region in which characteristic information of the object is to be acquired, and in terms of at least the number of times a receiver is scanned in a first direction, the receiver being configured to receive an acoustic wave from the object to acquire the characteristic information.

According to the present invention, in the operation of scanning a receiver while receiving an acoustic wave to acquire characteristic information, when a user defines a specified region to be scanned to acquire the characteristic information, a guide is displayed in terms of at least the number of times the receiver is scanned in one direction such that the user is allowed to easily recognize at least the number of times the receiver is scanned in one direction.

Further features of the present invention will become apparent from the following description of exemplary embodiments with reference to the attached drawings.

DESCRIPTION OF THE EMBODIMENTS

Figure 1:
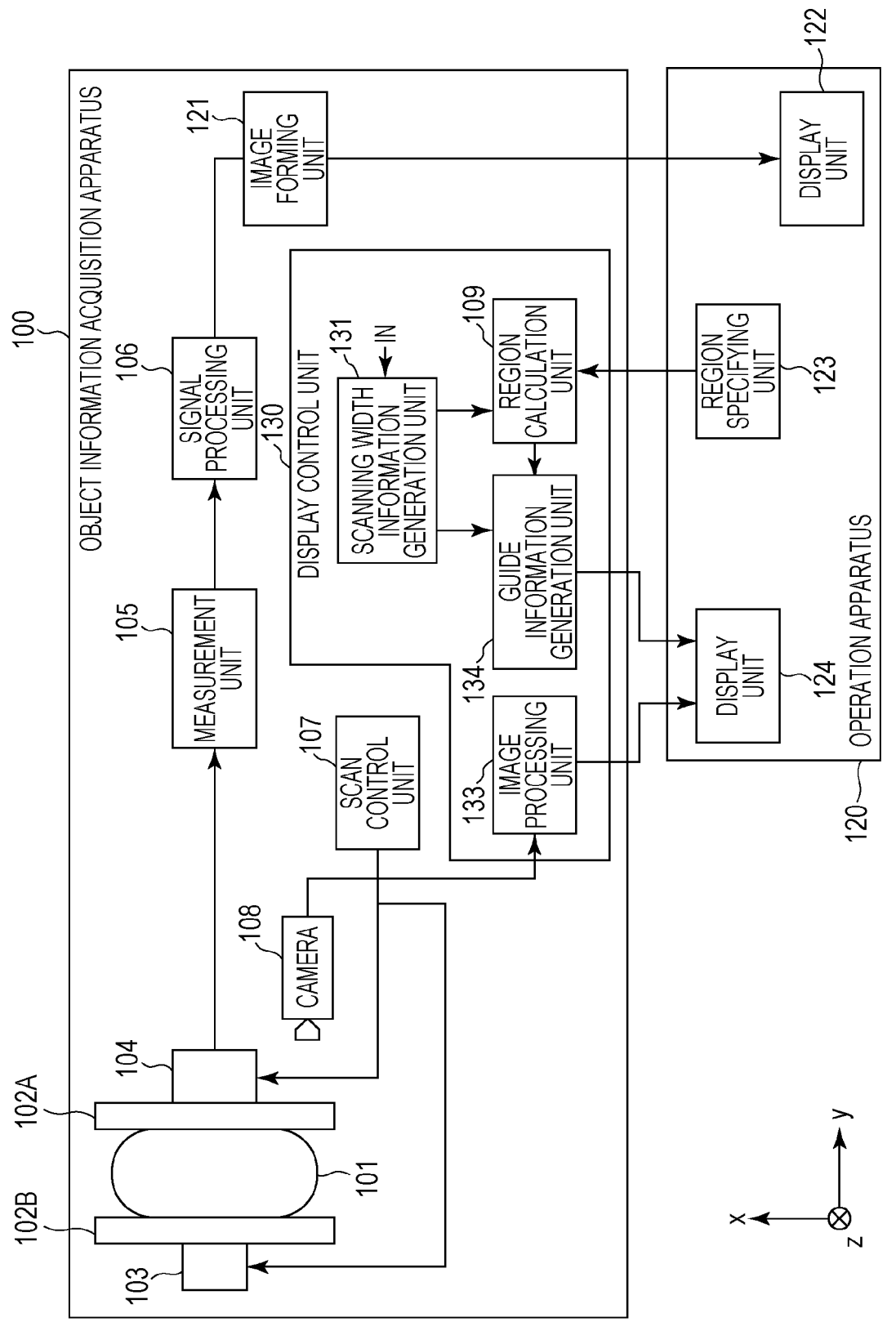
FIG. 1 is a block diagram of an object information acquisition apparatus according to an embodiment.

A basic idea of the present invention is based on a fact that when a region is specified by a user, a corresponding scanning region that needs to be scanned by a receiver depends on the number of times the receiver is scanned. According to embodiments of the invention, as will be described in detail below, when a user defines a specified region to be scanned to acquire the characteristic information, a guide is displayed in terms of at least the number of times the receiver is scanned in one direction.

In the embodiments of the present invention, the acoustic wave may be an elastic wave such as a sonic wave, an ultrasonic wave, a photoacoustic wave, a photo-ultrasonic wave, or the like, and the receiver receives the acoustic wave propagating through the object. That is, the object information acquisition apparatus includes an apparatus using a photoacoustic effect configured to illuminate an object with light (an electromagnetic wave) thereby generating an acoustic wave in the object, and receive the generated acoustic wave thereby acquiring characteristic information in the object. In the case of the apparatus using the photoacoustic effect, examples of acquired characteristic information in the object include an initial sound pressure of an acoustic wave generated by illumination of light, an absorption density or an absorption coefficient of photo energy determined from the initial sound pressure, object information depending on a content or the like of a substance forming a tissue, etc. Examples of substance contents include an oxygen saturation, oxy/deoxyhemoglobin content, etc. The characteristic information may be acquired in the form of numerical data, or the characteristic information may be acquired in the form of a characteristic distribution at various positions in the object, i.e., in the form of image data indicating a distribution in terms of an absorption coefficient, an oxygen saturation, etc.

In the embodiments of the invention, the object information acquisition apparatus may be implemented as an apparatus using an ultrasonic wave echo technique configured to transmit an ultrasonic wave to an object and receive a reflected wave from the inside of the object thereby acquiring characteristic information of the inside of the object. In the case of the apparatus using the ultrasonic wave echo technique, the characteristic information to be acquires is information in which a difference in acoustic impedance of a tissue inside the object is reflected.

Specific embodiments of the invention are described below with reference to drawings. Note that similar constituent parts are denoted by similar reference numerals or symbols, and duplicated explanations are not given.

First Embodiment

In a first embodiment, an apparatus using a photoacoustic effect is disclosed. The apparatus includes a receiver scanned in a main scanning direction and a sub scanning direction. When a user defines a region (specified region) to be scanned to acquire the characteristic information, a guide is displayed in terms of the number of times the receiver is scanned in a sub scanning direction. In the following description, a basic configuration and the apparatus and functions thereof are first explained. Thereafter, a method of defining the specified region and a display control method including features of the embodiment of the invention are explained.

Basic Configuration of Apparatus

FIG. 1 is a schematic diagram illustrating a configuration of an object information acquisition system including an object information acquisition apparatus 100 and an external operation apparatus 120 according to the first embodiment.

The object information acquisition apparatus 100 according to the present embodiment includes a holding unit 102 configured to hold a living body 101 given as an object, an illumination unit 103 configured to emit illumination light, a receiver 104 configured to receive an acoustic wave and convert it into a reception signal, and a measurement unit 105 configured to amplify the reception signal and convert it into a digital signal. The object information acquisition apparatus 100 further includes a signal processing unit 106 configured to perform a cumulative addition process or the like on the reception signal converted into the digital signal, an image forming unit 121 configured to generate image data using an output signal provided from the signal processing unit 106, a display control unit 130, a scan control unit 107 configured to control the scanning of the receiver 104, and a camera 108 serving as an image capturing unit.

The operation apparatus 120 includes a display unit 124 configured to display a captured image, a region specifying unit 123 for use by a user to define a specified region, and a display unit 122 configured to display an image generated by the image forming unit 121.

Elements of the object information acquisition apparatus 100 are described in further detail below.

Holding Unit

The holding unit 102 includes a pair of a first holding unit 102A and a second holding unit 102B between which a living body 101 such as a breast is put and held from both sides of the living body 101. The relative positions of these two holding units 102A and 102B are controlled by a holding mechanism (not shown) to adjust a holding distance and a holding pressure. In the following description, the holding units 102A and 102B are generically denoted as the holding unit 102 unless it is necessary to distinguish between them.

By firmly holding the living body 101 with the holding unit 102, it is possible to reduce a measurement error caused by motion of the living body 101. Furthermore, use of the holding unit 102 makes it possible to properly adjust the thickness of the living body 101 depending on a penetration depth of light. The holding unit 102 is located in the middle of an optical path, and thus the holding unit 102 may be formed using a material such as polymethylpentene or the like highly transparent to light used. The holding unit 102A located closer to the receiver 104 may be formed of a material that provides good acoustic matching with the receiver 104.

Illumination Unit

The illumination unit 103 that illuminates the living body 101 with light includes a light source configured to emit light, and an illumination part configured to guide the light emitted from the light source to the object such that the object is illuminated with the light. As for the light source, a solid-state laser may be used which is capable of emitting pulsed light (with a pulse width equal to or less than 100 nsec) having a center wavelength in a near-infrared range from 530 to 1300 nm. Examples of such solid-state lasers include a Yttrium-Aluminium-Garnet laser, a Titan-Sapphire laser, etc. The wavelength of light may be selected in a range from 530 nm to 1300 nm depending on a light absorbing substance (such as hemoglobin, glucose, cholesterol, etc.) in the living body to be examined. Examples of the illumination part include an optical reflection mirror, a lens that focuses or expands light or changes a shape of light, a prism that disperses, refracts, or reflects light, an optical fiber that transmits light, a diffusion plate, etc. Any illumination part may be used as long as it is capable of illuminating a desired area of the object with light with a desired form emitted from the light source. The position of a light emerging end of the illumination part (i.e., illumination area) is controlled by the scan control unit 107.

Receiver

The receiver 104 includes a plurality of elements for receiving an acoustic wave from the object and converting it into an electric signal (reception signal). Examples of devices usable as elements of the receiver 104 include for example, a transducer using a piezoelectric effect, a transducer using optical resonance, a transducer using a change in electrostatic capacitance, etc. Any type of device may be used as elements as long as it is capable of receiving an acoustic wave and converting it into an electric signal. The sound pressure of the generated acoustic wave is proportional to the intensity of light. Therefore, the signal-to-noise ratio (SNR) of the reception signal may be increased by employing a configuration in which light illuminates a front region of the receiver. Therefore, the illumination unit 103 and the receiver 104 may be located such that the light emerging end of the illumination unit 103 opposes the receiver 104 via the object. The scan control unit 107 may synchronously perform scanning such that the positional relationship between the light emerging end and the receiver 104 is maintained. The illumination part may guide light such that the living body 101 is also illuminated from the side of the receiver 104.

Measurement Unit

The measurement unit 105 includes a signal amplifier that amplifies an analog signal (analog reception signal) input from the receiver 104, and an analog-to-digital converter that converts the analog signal into a digital signal. The signal amplifier controls a gain depending on a time since the object is illuminated with light till the acoustic wave reaches the elements of the receiver so that uniform contrast is obtained regardless of the depth in the object (living body).

Signal Processing Unit

The signal processing unit 106 performs processes including correcting difference among elements in terms of sensitivity to the digital reception signal output from the measurement unit 105, making up for a lost signal due to a physical or electric defect of an element, storing the signal in a storage medium (not shown), cumulatively adding signals to reduce noise, etc. In the cumulative addition process, an acoustic wave from the living body 101 is received repeatedly at the same scanning position and the received signal is cumulatively added and averaged thereby reducing system noise. This makes it possible to obtain a reception signal with improved SNR.

Image Forming Unit

The image forming unit 121 serves as a characteristic information acquisition unit that acquires image data representing a distribution of optical characteristic information (absorption coefficient, oxygen saturation, etc.) at various locations in the living body 101 using a signal output from the signal processing unit 106. The generated image data may be subjected, as required, to various correction processes such as luminance adjustment, distortion correction, clipping of a particular region of interest, etc., to obtain image data more suitable for diagnosis. Furthermore, to reduce noise, characteristic information at the same location may be subjected to a cumulative addition process. The display unit 122 receives the image data from the image forming unit 121 and displays an image of the characteristic distribution based on the received image data.

Scan Control Unit

As described above, the scan control unit 107 is a unit configured to control the light emerging end and the scanning position of the receiver 104. By performing two-dimensional scanning on the living body 101 and receiving acoustic waves at respective scanning positions, it is possible to obtain characteristic information over a wide range even when the receiver is of a small type. In the present embodiment, the scanning of the receiver is not limited to the two-dimensional scanning but the scanning may be performed in other manners as long as the receiver is scanned at least in one direction. The scan control unit 107 may change the scanning region depending on a result of controlling of the display control unit 130.

Image Capturing Unit

The camera 108 serving as the image capturing unit is for capturing an image of the living body 101 and is installed such that its line-of-sight direction is perpendicular to the holding unit 102 for holding the living body 101. The captured image is transmitted to the display unit 124 via a captured image processing unit 133. The field of view of the camera 108 may be set such that the captured image covers the whole region scannable by the receiver 104. The captured image is displayed on the display unit 124 such that a user is allowed to refer to the captured image displayed on the display unit 124 during the operation of specifying a region (specified region) in which characteristic information is to be acquired. In the present embodiment, the display unit 124 is provided separately from the display unit 122 for displaying an image of characteristic information. However, alternatively, the image for use in defining the specified region and the image of characteristic information may be displayed on a single display unit.

Region Specifying Unit

The region specifying unit 123 is an input unit for use by a user to define a specified region. The user is allowed to input a specified region 201 (see FIG. 2) while referring to a captured image of the living body 202 displayed on the display unit 124. Specific examples of the region specifying unit 123 include a pointing device such as a mouse, a keyboard, or the like, a tablet-type device, a touch pad attached to a surface of the display unit 124, etc.

Display Control Unit

The display control unit 130 receives information associated with the specified region defined by a user, and generates guide information that is information (display information) for displaying a guide on a display unit in terms of the number of times the receiver at least in one direction. In the present embodiment, the display control unit 130 includes a region calculation unit 109 configured to receive information associated with the specified region and determine a corresponding scanning region, and a guide information generation unit 134 configured to generate guide information. The display control unit 130 according to the present embodiment also includes a captured image processing unit 133 configured to output image data captured by the camera to the display unit 124. In the present embodiment, it is assumed by way of example that the first direction is the sub scanning direction and the second direction is the main scanning direction. Note that in the present embodiment, the main scanning direction is a direction in which the receiver is scanned while receiving an acoustic wave at each reception position, and the sub scanning direction is a direction perpendicular to the main scanning direction.

In the present embodiment, when the region calculation unit 109 receives information associated with the specified region 201 defined by the region specifying unit 123, the region calculation unit 109 converts the expression of the specified region from the display coordinate system into the scanning coordinate system, and the region calculation unit 109 calculates a scanning region that needs to be scanned by the receiver to acquire characteristic information of the specified region. The scanning region will be described in further detail later with reference to FIG. 5.

In the present embodiment, based on the information associated with the scanning region, the guide information generation unit 134 generates guide information for displaying a guide in terms of the number of times scanning in the sub scanning is performed. In embodiments of the present invention, specific examples of guides in terms of the number of times scanning is performed include a guide given by text indicating the number of times the receiver is canned (see FIG. 6B), a guide given by lines indicating a scanning width of the receiver (see FIG. 6A), etc. In the second example of the guide, the number of times scanning is performed corresponds to the number of lines indicating scanning width. Therefore, for example, an increase by one in the number of lines indicates that an increase by one in the number of times scanning is performed. Note that the guide in terms of the number of times scanning is performed is not limited to the two examples described above, but any type of information may be used as long as it indicates the number of times scanning is performed or a change in the number of times scanning is performed.

In the present embodiment, the display control unit 130 may include a scanning-width information generation unit 131 configured to determine a scanning width. In a case where the sub-scanning width and the main scanning width are fixed, the display control unit 130 does not necessarily need to include the scanning-width information generation unit 131. However, the sub-scanning width and the main scanning width may vary depending on the number of operations of cumulatively adding reception signals to improve the SNR or the number of operations of combining characteristic information (image data). Therefore, in accordance with such setting for improving SNR, the scanning-width information generation unit 131 determines the scanning width and transmits information associated with the scanning width to the region calculation unit 109 and the guide information generation unit 134 as will be described in further detail later.

The display control unit 130 transmits the generated guide information to the display unit 124 in the above-described manner to display the guide in terms of the number of times scanning is performed. When a specified region is being defined, for example, by dragging a mouse, the display control unit 130 may display the guide indicating the number of times scanning should be performed to obtain characteristic information for the specified region being defined. Displaying the guide in such a manner makes it possible for a user to recognize a change in the number of scans of the receiver that may occur due to a slight change in the size of the specified region 201 being defined. Therefore, the user is allowed to determine a final specified region based on the number of scans displayed for the current specified region or the specified region being changed in the middle of the process of defining the specified region. The flow of the control process performed by the display control unit 130 will be described in further detail below with reference to FIG. 4.

The configuration of the object information acquisition system according to the present embodiment has been described above. Note that in the example shown in FIG. 1, the operation apparatus 120 is installed externally, and the object information acquisition apparatus 100 is implemented by hardware separate from the operation apparatus 120, these apparatuses may be integrated into a single apparatus.

Method of Defining Specified Region

Figure 2:
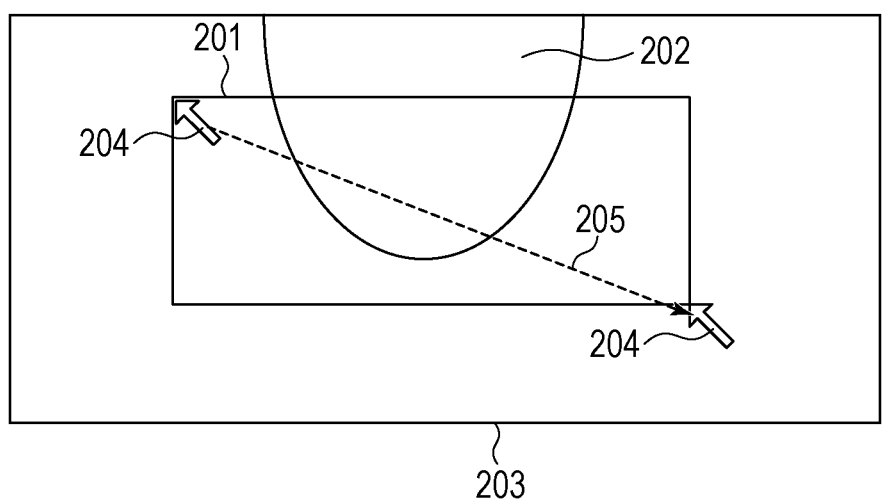
FIG. 2 is a conceptual diagram illustrating a method of defining a specified region according to an embodiment.
Figure 3:
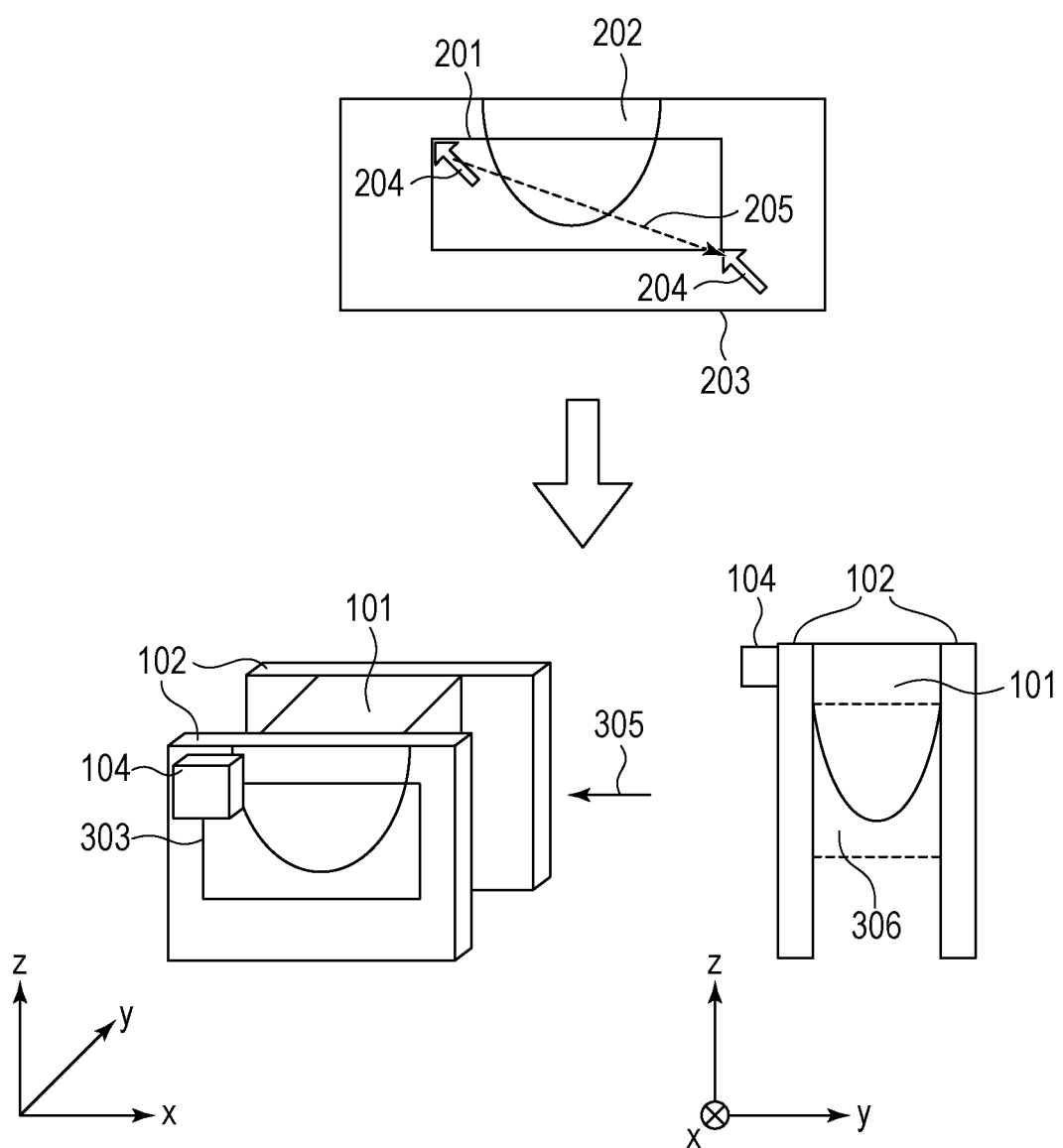
FIG. 3 is a conceptual diagram illustrating an example of a three-dimensional region corresponding to a specified region according to an embodiment.

A method of defining a specified region according to the present embodiment is described below. In the present embodiment, a signal of an acoustic wave generated inside a living body is also acquirable, and thus a characteristic distribution may be acquired not only in the form of a two-dimensional image (tomographic view) but also in the form of a three-dimensional image. FIG. 2 is a conceptual diagram illustrating a method of defining a specified region on a display screen in a process of acquiring a three-dimensional image. FIG. 3 is a conceptual diagram illustrating a three-dimensional region corresponding to a specified region in a living body.

As shown in FIG. 2, a user may define a two-dimensional rectangle on the display screen 203 on which a captured image is displayed thereby defining a specified region 201 to be scanned to acquire characteristic information. In the present embodiment, a mouse is used as the region specifying unit 123. A user is allowed to operate a cursor 204 to input a rectangle thereby defining the region with an arbitrary size. The user is allowed to view the captured image of the living body 202 during the operation of defining the specified region 201 on the display screen. This makes it easy for the user to correctly input the specified region 201 as is intended.

In FIG. 3, a region 303 is a specified region of the receiver 104 expressed in a scanning coordinate system corresponding to the specified region 201 expressed in a display coordinate system. A conceptual diagram in the lower-right part of FIG. 3 is a view of the lower-left diagram seen in a direction denoted by an arrow 305. A three-dimensional specified region 306 is a region in which characteristic information is acquirable by scanning the receiver over the scanning region 303. The three-dimensional specified region 306 is determined by a distance between the holding units 102. During a measurement operation, the distance between the holding units 102 is maintained at a fixed value. When the specified region 201 is defined in the display coordinate system on the display screen as described above, the three-dimensional region 306 in an actual living body is determined. That is, defining the specified region 201 in the display coordinate system results in defining the three-dimensional specified region 306 in the three-dimensional coordinate system.

In the following description, it is assumed by way of example that the three-dimensional specified region 306 is defined by defining a rectangular region (the specified region 201 in the display coordinate system) using a mouse. Note that the three-dimensional specified region 306 may be defined by other methods. For example, the specified region 303 in the scanning coordinate system and the distance between the holding units 102 may be separately defined by using separate region specifying units.

The specified region 201 is not limited to a rectangle region, but a region of any other shape such as a circle, an ellipse, a polygon, etc. may be specified. More specifically, for example, when a rectangle is specified using a mouse, a circle, an ellipse, or a polygon inscribed in the rectangle may be specified as the specified region 201. The specified region 201 may be defined by two points specified using a mouse. More specifically, for example, when the mouse is dragged such that a cursor 204 moves along a trajectory 205 from an upper-left point to a lower-right point, a rectangle defined by these two points may be employed as the specified region 201. In the case where the specified region 201 is defined by a rectangle, a three-dimensional region whose one surface corresponds to the specified region 201 may be employed as the three-dimensional specified region 306. Thus, by dragging the mouse in the above-described manner, it is possible to determine the size of the specified region 201 and the size of the three-dimensional specified region 306.

Flow of Display Control Method

Figure 4:
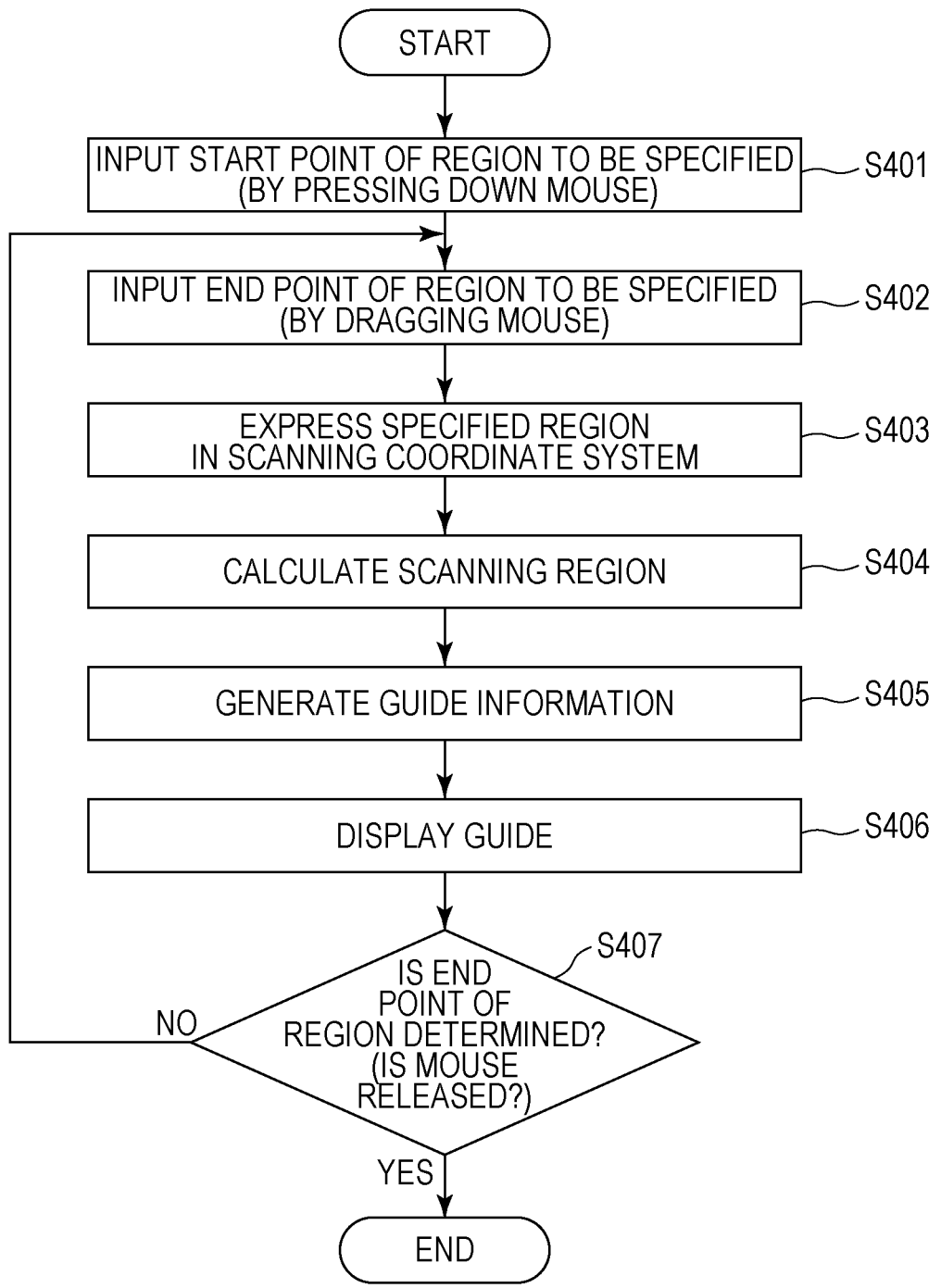
FIG. 4 is a flow chart illustrating an example of a display control method according to an embodiment.

Referring to FIG. 4, a display control process according to the present embodiment is described below. FIG. 4 is a flow chart of the display control process according to the present embodiment.

After the apparatus is started, the process shown in the flow chart of FIG. 4 starts from a state in which a user inputs a specified region on the display screen on which an image of the living body 101 captured in a particular direction is displayed. That is, the display control method according to the present embodiment includes a step of first displaying a captured image of an object. In the present embodiment, a mouse is used as the region specifying unit 123.

In step S401, if a user presses down a mouse button at a particular point on the display screen, then this point is input as a start point of the specified region 201. In step S402, if the user changes the size of the specified region 201 by dragging the mouse, the position of the mouse cursor at this point of time is input as an end point of the specified region 201, and thus the specified region 201 as of this point of time is defined.

In step S403, on receiving the information associated with the specified region 201, the region calculation unit 109 converts the received expression of the specified region 201 from the display coordinate system into the scanning coordinate system of the receiver. Furthermore, in step S404, based on the information associated with the specified region 303 in the scanning coordinate system, the scanning region of the receiver in the scanning coordinate system is determined. Note that the method of determining the scanning region of the receiver in the scanning coordinate system is not limited to the method of determination from the specified region 303 in the scanning coordinate system. For example, the three-dimensional specified region 306 may be determined based on the specified region 201 in the display coordinate system, and the scanning region of the receiver in the scanning coordinate system may be determined based on the three-dimensional specified region 306.

Figure 5:
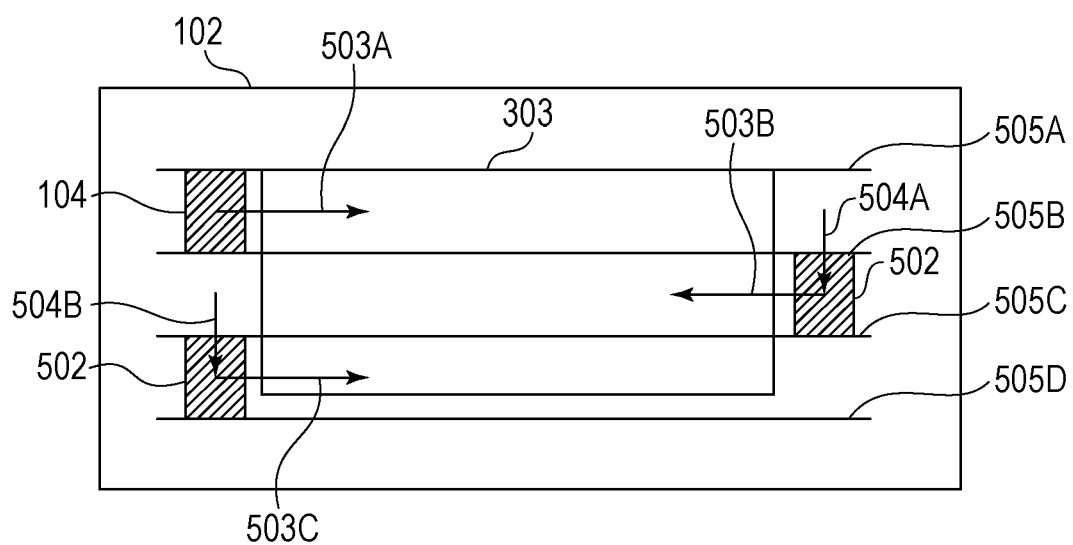
FIG. 5 is a conceptual diagram illustrating a scanning region according to a first embodiment.

The scanning region is described in further detail below with reference to FIG. 5. FIG. 5 is a conceptual diagram illustrating a scanning region that is to be scanned by the receiver 104 to acquire characteristic information of the specified region 303 in the scanning coordinate system. In the determination of the scanning region, in addition of the information associated with the specified region, the information associated with the scanning width is used. In the following description, it is assumed by way of example that the scanning width of the receiver 104 in the sub scanning direction is equal to the size (length) of the receiver 104 in the sub scanning direction. Note that the size of the receiver 104 is assumed to be equal to the size of an effective element array region including a plurality of elements each configured to output a reception signal from which to generate image data.

For example, in a case where the size of the receiver 104 in the sub scanning direction is equal to 5 cm, if main scanning is performed over one stripe, then characteristic information is obtained for the stripe with a width of 5 cm as measured in the sub scanning direction. Note that the width of sub scanning (504A and 504B in the example shown in FIG. 5) of the receiver is also 5 cm which is equal to the size of the receiver 104 in the sub scanning direction. Hereinafter, each region that is scanned in the main scanning direction while receiving an acoustic wave is referred to as a stripe. The sub-scanning width may be determined in advance or information associated with the scanning width may be given as required from the scanning-width information generation unit 131.

A width between a line 505A and a line 505B, a width between the line 505B and a line 505C, and a width between the line 505C and a line 505D respectively indicate scanning widths in the sub scanning direction, i.e., each of these scanning widths indicates one stripe of main scanning region. In a case where the length of the specified region 303 in the sub scanning direction expressed in the scanning coordinate system is, for example, 13 cm, the receiver 104 needs to perform main scanning for three stripes (that is, it is necessary to perform sub scanning two times) to acquire characteristic information of the region with the above-described size. Thus, in this case, the length of the scanning region in the sub scanning direction is 15 cm. The length of the scanning region in the direction of main scans (503A, 503B, and 503C) is also calculated based on the scanning width in the main scanning direction. Thus, the scanning region of the receiver is determined in the above-described manner. In the example described above, it is assumed by way of example that the size of the receiver in the sub scanning direction is equal to 5 cm. Note that the scanning region can be calculated regardless of the scanning width of the receiver.

As a result of the calculation of the scanning region performed by the region calculation unit 109, the number of scans performed by the receiver is also determined. Thus, in a next step S405, based on the scanning region of the receiver, the guide information generation unit 134 generates guide information for displaying a guide in terms of the number of scans performed by the receiver at least in one direction (in the sub scanning direction in the present example). In step S406, the guide is displayed on the display unit 124. Examples of displayed guides are shown in FIG. 6A and FIG. 6B.

Figure 6A:
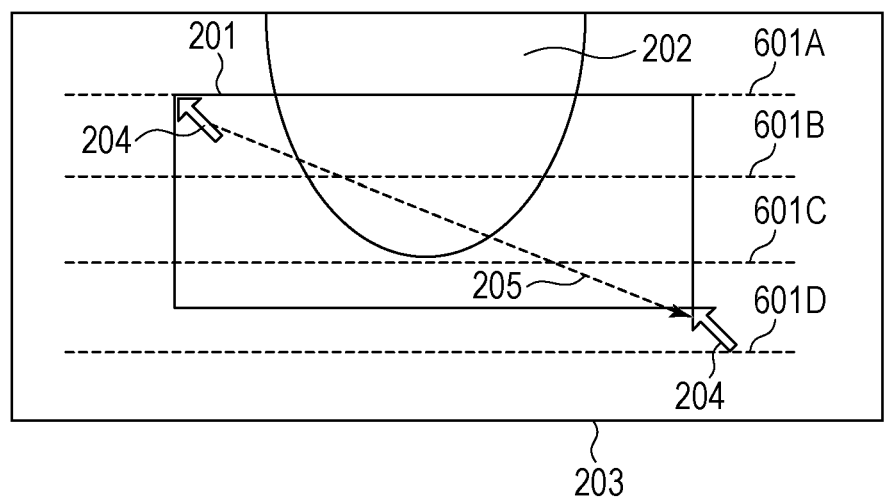
FIG. 6A is a conceptual diagram illustrating an example of a guide in the form of lines according to the first embodiment.

In the example shown in FIG. 6A, lines (601A, 601B, 601C, and 601D) indicating sub-scanning widths are displayed as a guide such that when a user defines the specified region 201, the user is allowed to know the number of scans performed by the receiver in the sub scanning direction. When the user inputs the specified region 201 by operating the cursor 204 while viewing the living body 202 displayed on the display screen 203, the user is allowed to know the number of scans in the sub scanning direction necessary for the specified region 201 defined by the user. In the case where lines are displayed to indicate the scanning widths as in the example described above, the positions and the sizes of the lines produced in step S406 are converted from the scanning coordinate system into the display coordinate system and transmitted to the display unit 124.

During the process of defining the specified region 201, i.e., in the state (mode) in which a user is allowed to define the specified region, not only the guide but the size of the specified region 201 may also be displayed. That is, the display control unit 130 may output display information for displaying the specified region. Displaying the size of the specified region 201 makes it possible for the user to recognize the relationship between the specified region 201 and the number of scans needed for the specified region 201 during the process of defining the specified region 201.

Figure 6B:
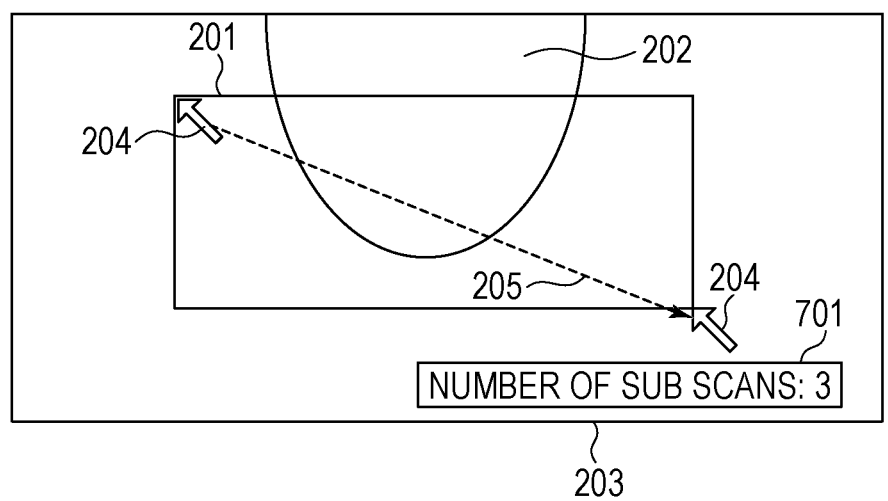
FIG. 6B is a conceptual diagram illustrating an example of a guide in the form of text according to the first embodiment.

On the other hand, in the example shown in FIG. 6B, guide information is generated and a guide is displayed according to the guide information in the form of text (701) to indicate the number of scans performed by the receiver in the sub scanning direction necessary for the defined specified region. Also in this case, the displaying of the size of the specified region 201 makes it possible for a user to recognize the relationship between the specified region 201 and the number of scans necessary for the specified region in the operation of defining the specified region 201.

In step S407, if the mouse button is released to finally determine the end point of the specified region 201, the specified region 201 is finally determined. In a case where it is determined in step S407 that the mouse button is not yet released, the processing flow returns to step S402 to repeat the process described above. Thus, whenever the user changes the size of the specified region 201 by dragging the mouse, the necessary scanning region of the receiver is changed and the guide in terms of the number of scans is displayed. That is, the guide information is updated according to the change in the size of the specified region, and the guide in terms of the number of scans is displayed whereby the user is allowed to recognize the necessary number of scans in real time.

In the above example, in the defining the rectangle, the start point defines the upper-left corner of the rectangle and the end point defines the lower-right corner of the rectangle. Alternatively, the start point may define the upper-right corner and the end point may define the lower-left corner of the rectangle. When the end point is specified, the specified region displayed is set as an acquisition region in which characteristic information is to be actually acquired by scanning the receiver. Thus, the object information acquisition apparatus 100 is allowed to acquire characteristic information of a three-dimensional region in the object corresponding to the set acquisition region.

In the processing flow described above, the scanning region of the receiver in the scanning coordinate system is calculated in step S404 based on the information associated with the specified region 303 in the scanning coordinate system. However, it does not necessarily need to calculate the scanning region. The guide information may be directly generated based on the specified region 303 in the scanning coordinate system.

In the processing flow described above, the guide information is generated after the specified region 201 is converted from the display coordinate system into the scanning coordinate system. Alternatively, the guide information may be generated based on the specified region 201 in the display coordinate system without performing the conversion into the scanning coordinate system. In this case, it is necessary to convert the expression of the scanning width from the scanning coordinate system into the display coordinate system.

Modified Example

A modified example of the first embodiment is described below. In this modified example, the scanning width of the receiver in the sub scanning direction is smaller than the length of the receiver in the sub scanning direction, and a scanning path of the receiver in the main scanning direction overlaps a scanning path in the sub scanning direction. In the present modified example, the object information acquisition system is configured in a similar manner to that shown in FIG. 1, and thus a further description thereof is omitted. The processing flow of the display control is basically similar to that shown in FIG. 3, although there is some difference in the process in step S404 and following S404 as described below.

Figure 7:
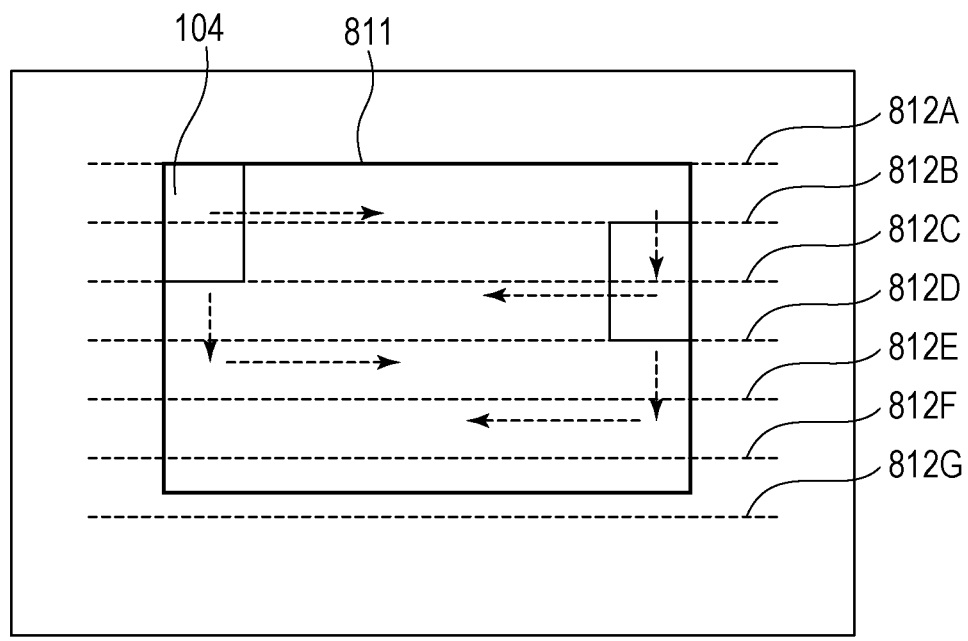
FIG. 7 is a conceptual diagram illustrating a scanning region according to a modified example of the first embodiment.

FIG. 7 is a conceptual diagram illustrating a scanning region. In this figure, lines 812A to 812G are for indicating scanning widths in the sub scanning direction. In the example shown in FIG. 7, it is assumed, by way of example, that the scanning width of the receiver 104 in the sub scanning direction is 2.5 cm, and the length of the receiver 104 in the sub scanning direction is 5 cm. In this example, it is further assumed that the size of the receiver 104 is equal to the size of the effective element array region in which a plurality of elements are disposed.

In a case where the length of the specified region 811 in the main scanning direction expressed in the scanning coordinate system is, for example, 13 cm, the receiver 104 needs to perform main scanning for five stripes (that is, it is necessary to perform sub scanning four times) to acquire characteristic information of the region with the above-described size. That is, in this case, the length of the scanning region in the sub scanning direction is 15 cm. Similarly, the length of the scanning region in the main scanning direction is also calculated based on the scanning width in the main scanning direction. That is, the guide information generation unit 134 receives information associated with the scanning width in the sub scanning direction, and generates guide information for displaying the guide on the display unit in terms of the number of scans.

In the present modified example, as described above, the sub-scanning width of the receiver is smaller than the length of the receiver in the sub scanning direction. This is for making it possible for the signal processing unit to cumulatively add a plurality of reception signals to improve SNR. More specifically, when two or more different elements of the plurality of elements of the receiver receive acoustic waves from the object at the same scanning position at different points of time, electric signals output from the respective two or more different elements are cumulatively added together. The scanning width of the receiver is determined by the number of cumulative addition operations for the plurality of reception signals (the number of times the cumulative addition operation is performed). The smaller the scanning width, the greater the overlapping of the scanning region. Therefore, the smaller the scanning width, the greater the number of cumulative addition operations and thus SNR is more improved. Alternatively, to improve SNR, characteristic information may be cumulatively combined instead of cumulatively adding reception signals. More specifically, each time sub scanning is performed, the image forming unit acquires characteristic information of one stripe using a plurality of electric signals output from a plurality of elements. The image forming unit combines together characteristic information of a plurality of stripes to acquire a characteristic distribution in the object. That is, the image forming unit combines (by means of addition, multiplication, etc.) characteristic information acquired at the same position in the object. The number of times characteristic information is combined determines the scanning width of the receiver. Note that it may be allowed to perform both the cumulative addition of reception signals and the cumulative combination of characteristic information.

Thus, when the scanning-width information generation unit 131 receives a command from a user in terms of the number of cumulative addition operations or the number of cumulative combination operations, the scanning-width information generation unit 131 determines the scanning width of the main scanning and that of the sub scanning. The information associated with the scanning width is transmitted to the region calculation unit 109 and the guide information generation unit 134.

The scanning trajectory described above with reference to FIG. 7 includes only one forward scan per one stripe. Alternatively, one stripe may be scanned in both forward and backward directions, or may be scanned a plurality of times. A stripe on the top and a stripe on the bottom are subjected to a less number of cumulative addition operations than the other stripes, and thus the number of scans may be increased for the stripe on the top and that on the bottom.

In the examples shown in FIG. 5 and FIG. 7, it is assumed that the size of the receiver 104 is equal to the size of the effective element array region in which a plurality of elements are disposed. However, the effective element array region may be smaller than the size of the receiver 104 (as in a case where dummy elements that do not use reception signals are disposed in a peripheral area). In such a case, the scanning width may be calculated based on the size of the effective element array region.

Second Embodiment

A second embodiment of the present invention is described below. In this second embodiment, a guide is displayed in terms of the scanning width in the main scanning direction in the specified region defined by a user. That is, in the following description of the present embodiment, it is assumed that the first direction is the main scanning direction and the second direction is the sub scanning direction.

In the present embodiment, the object information acquisition system is configured in a similar manner to that according to the first embodiment, although there is a difference in function of the display control unit 130. Thus, a further description of similar parts to those in the first embodiment is omitted, and the following description focuses on differences from the first embodiment. The processing flow of the display control is similar to that according to the first embodiment described above with reference to FIG. 4, although there is some difference in the process in step S403 and following S403 as described below.

Figure 8:
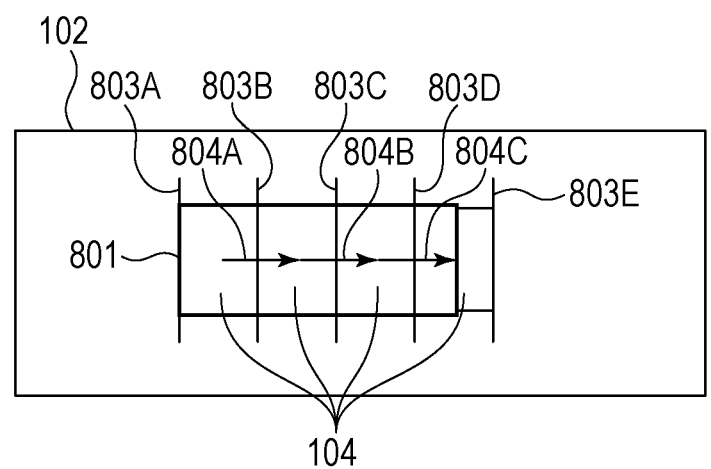
FIG. 8 is a conceptual diagram illustrating a scanning region according to a second embodiment.

First, in the region calculation unit 109, a specified region 2 defined on a captured image by using the region specifying unit 123 is converted from the display coordinate system into the scanning coordinate system (step S403). FIG. 8 is a conceptual diagram illustrating an example of a scanning region.

In the example shown in FIG. 8, the scanning width of the receiver 104 in the main scanning direction is equal to the length of the receiver 104 in the main scanning direction. The receiver 104 receives an acoustic wave at each scanning position. Note that the size of the receiver 104 is equal to the size of the effective element array region. In FIG. 8, a width (distance) between a line 803A and a line 803B, a width (distance) between the line 803A and a line 803C, a width (distance) between the line 803C and a line 803D, and a width (distance) between the line 803D and a line 803E respectively indicate scanning widths in the main scanning direction. For example, when the size of the receiver 104 in the main scanning direction is 5 cm, the scanning width (804A, 804B, and 804C) of the receiver in the main scanning direction is also equal to 5 cm. The scanning width may be determined in advance or may be determined as required according to information on the scanning width generated by the scanning-width information generation unit 131.

In a case where the length of the specified region 801 in the main scanning direction expressed in the scanning coordinate system is, for example, 18 cm, to acquire characteristic information of the region with this size, acoustic waves are received while shifting the scanning position of the receiver in the main scanning direction. More specifically, the main scanning of the receiver is performed three times, and thus acoustic waves are received at four different scanning positions. In this case, sub scanning is not necessary. The scanning region of the receiver is calculated in the above-described manner (step S404). Note that also in a case where the scanning width of the receiver 104 in the main scanning direction is not equal to the size of the receiver 104 in the main scanning direction, it is possible to calculate the scanning region of the receiver based on the main scanning width.

As a result of the calculation of the scanning region performed by the region calculation unit 109, the number of scans performed by the receiver is also determined. Thus, in a next step S405, the guide information generation unit 134 generates guide information for displaying a guide in terms of the number of scans performed by the receiver in the main scanning direction. In step S406, the guide in terms of the number of scans is displayed on the display unit 124. Examples of displayed guides are shown in FIG. 9A and FIG. 9B.

Figure 9A:
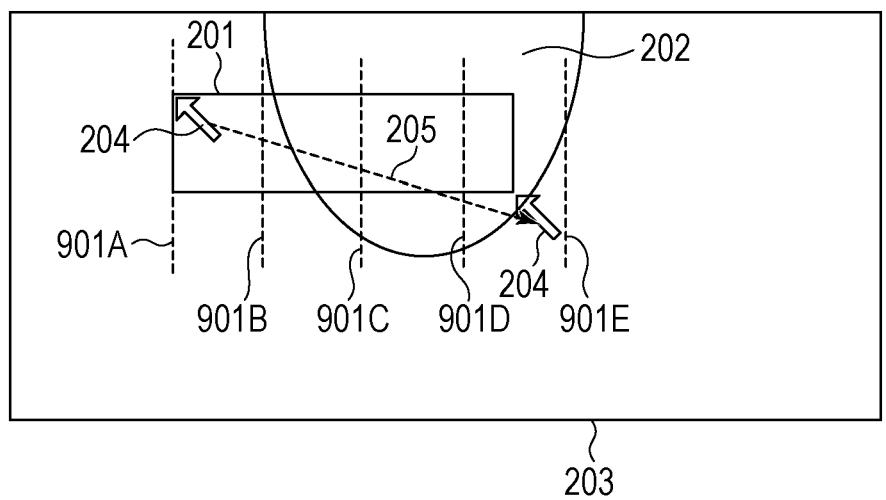
FIG. 9A is a conceptual diagram illustrating an example of a guide in the form of lines according to the second embodiment.

In the example shown in FIG. 9A, lines (901A, 901B, 901C, and 901D) indicating main scanning widths are displayed as a guide such that when a user defines the specified region 201, the user is allowed to know the number of scans performed by the receiver in the main scanning direction. When the user inputs the specified region 201 by operating the cursor 204 while viewing the living body 202 displayed on the display screen 203, the user is allowed to know the number of scans in the main scanning direction necessary for the specified region 201 defined by the user. In the case where lines are displayed to indicate the scanning widths as in the example described above, the positions and the sizes of the lines produced in step S406 are converted from the scanning coordinate system into the display coordinate system and transmitted to the display unit 124.

During the process of defining the specified region 201, i.e., in the state (mode) in which a user is allowed to define the specified region, the size of the specified region 201 may also be displayed. Displaying the size of the specified region 201 makes it possible for the user to recognize the relationship between the specified region 201 and the number of scans needed for the specified region 201 during the process of defining the specified region 201.

Figure 9B:
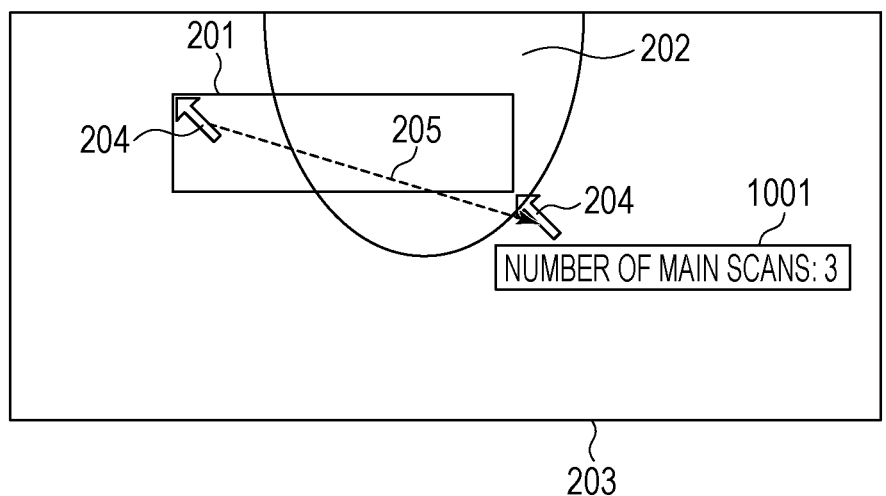
FIG. 9B is a conceptual diagram illustrating an example of a guide in the form of text according to the second embodiment.

On the other hand, in the example shown in FIG. 9B, a guide is displayed in the form of text (1001) to indicate the number of scans performed by the receiver in the main scanning direction necessary for the defined specified region 201. Also in this case, the displaying of the size of the specified region 201 makes it possible for a user to recognize the relationship between the specified region 201 and the number of scans in the main scanning direction necessary for the specified region 201 in the operation of defining the specified region 201.

In step S407, if the mouse button is released to finally determine the end point of the specified region 201, the specified region 201 is finally determined. In a case where it is determined in step S407 that the mouse button is not yet released, the processing flow returns to step S402 to repeat the process described above. Thus, whenever the user changes the size of the specified region 201 by dragging the mouse, the necessary scanning region of the receiver is changed and the guide in terms of the number of scans is displayed. That is, the guide information is updated according to the change in the size of the specified region, and the guide in terms of the number of scans is displayed whereby the user is allowed to recognize the necessary number of scans in real time.

In the present example, in the defining the rectangle, the start point defines the upper-left corner of the rectangle and the end point defines the lower-right corner of the rectangle. Alternatively, the start point may define the upper-right corner and the end point may define the lower-left corner of the rectangle. When the end point is specified, the specified region displayed is set as an acquisition region in which characteristic information is to be actually acquired by scanning the receiver. The scanning of the receiver may be performed in a step-and-repeat manner in which the receiver stops at each scanning position, receives an acoustic wave, and then moves to a next scanning position. Note that, in the main scanning direction, the receiver may be continuously moved at a constant speed. In a case where the receiver is continuously scanned, each scanning position is defined as a position where the receiver is located when light is irradiated. The number of strokes of main scanning is defined by the number of times the receiver moves from one scanning position to a next scanning position in one stripe. Thus, the object information acquisition apparatus 100 is allowed to acquire characteristic information of a three-dimensional region in the object corresponding to the set acquisition region.

In the processing flow described above, the scanning region of the receiver in the scanning coordinate system is calculated in step S404 based on the information associated with the specified region 303 in the scanning coordinate system. However, it does not necessarily need to calculate the scanning region. The guide information may be directly generated based on the specified region 303 in the scanning coordinate system.

In the processing flow described above, the guide information is generated after the specified region 201 is converted from the display coordinate system into the scanning coordinate system. Alternatively, the guide information may be generated based on the specified region 201 in the display coordinate system without performing the conversion into the scanning coordinate system. In this case, it is necessary to convert the expression of the scanning width from the scanning coordinate system into the display coordinate system.

Also in the present embodiment, as in the modified example of the first embodiment, the receiver may be scanned in the main scanning direction at overlapping scanning positions and a plurality of reception signals may be cumulatively added together to improve SNR. That is, the present embodiment may also be applied to a case in which the scanning width of the receiver in the main scanning direction is smaller than the length of the receiver in the main scanning direction. In the display control processing, as in the modified example of the first embodiment, the scanning-width information generation unit 131 generates information associated with the scanning width of the main scanning in accordance with a command issued by a user in terms of the number of times reception signals are cumulatively added, the number of times characteristic information (image data) is cumulatively combined, etc. The generated information is transmitted to the region calculation unit 109 and the guide information generation unit 134. By overlapping scanning positions in the main scanning direction in the above-described manner, it becomes possible for the object information acquisition apparatus 100 to acquire image data with improved SNR.

Third Embodiment

The guide displayed may include both information in terms of the number of scans in the main scanning direction and information in terms of the number of scans in the sub scanning direction, necessary for a specified region. In a third embodiment, to provide guide information for displaying on the display unit in terms of the guide indicating the number scans in both the main scanning direction and the sub scanning direction, the function of the region calculation unit 109 and the function of the guide information generation unit 134 according to the first embodiment and those according to the second embodiment are combined.

The region calculation unit 109 calculates the scanning region of the receiver based on the information associated with the specified region. After the guide information generation unit 134 generates the guide information in the sub scanning direction in a similar manner to the first embodiment, the guide information generation unit 134 generates the guide information in the main scanning direction in a similar manner to the second embodiment. The guide information generation unit 134 transmits both pieces of generated guide information to the display unit 124 to display them.

By displaying the guide in terms of the number of scans in the main scanning direction and the guide in terms of the number of scans in the sub scanning direction necessary for the specified regions defined by the user, it becomes possible for the user to recognize the number of scans that needs to be performed by the receiver for the specified region. This makes it possible to reduce the possibility that a slight difference in the specified region results in an unnecessary increase in the number of strokes of scanning of the receiver, which may create a redundant time period in the acoustic wave reception time period for acquiring characteristic information, which may in turn redundantly increase a time period during which a person under examination is constrained.

Fourth Embodiment

In the first to third embodiments described above, the object information acquisition apparatuses and systems are disclosed which are based on the photoacoustic effect, that is, which acquire object information by illuminating object with light and receiving an acoustic wave generated in the object. Alternatively, an object information acquisition apparatus or a system may be realized using an ultrasonic wave echo. In this case, an ultrasonic wave is transmitted toward an object, and the ultrasonic wave reflected back from the inside of the object is received as an acoustic wave by a receiver. In the case of an apparatus using an ultrasonic wave echo, the receiver may be configured such that it also functions as a transmitter that transmits an ultrasonic wave to an object.

Fifth Embodiment

The present invention may be practiced by executing the following processing. That is, software (program) for implementing the functions disclosed in the embodiments is provided to a system or an apparatus via a network or a storage medium, and a computer (or a CPU or an MPU) in the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-172975 filed Aug. 8, 2011 and No. 2012-156630 filed Jul. 12, 2012, which are hereby incorporated by reference herein in their entirety.

What is claimed is:

1. An object information acquisition apparatus, comprising:
   a receiver configured to receive an acoustic wave from an object and convert the received acoustic wave into an electric signal;
   a moving control unit configured to move the receiver at least in a first direction and a second direction which is a direction perpendicular to the first direction;
   a characteristic information acquisition unit configured to acquire, using the electric signal, characteristic information on the object; and
   a display control unit configured to:
      receive specified region information associated with a specified region defined by a user,
      produce, using the specified region information, guide information in terms of a number of times the receiver is moved in the first direction for acquiring the characteristic information on the object in the specified region, and
      cause a display unit to display a guide based on the guide information,
   wherein the information acquisition unit is configured to acquire, using the electric signal, the characteristic information on the object in the specified region.

2. The object information acquisition apparatus according to claim 1, wherein:
   the receiver includes a plurality of elements each configured to receive the acoustic wave and convert the received acoustic wave into an electric signal; and
   the display control unit determines a movement width of the receiver in the first direction based on the number of times cumulative addition is performed on electric signals which are output from two or more respective different elements when acoustic waves from the object are received at the same movement position at different points of time, and the display control unit generates the guide information using information associated with the specified region and information associated with the movement width.

3. The object information acquisition apparatus according to claim 1, wherein
   the receiver includes a plurality of elements each configured to receive the acoustic wave and convert the received acoustic wave into an electric signal, wherein the object information acquisition apparatus further comprises a characteristic information acquisition unit configured to acquire characteristic information of one stripe using the plurality of electric signals output from the plurality of elements each time a first movement in the first direction is performed and combine characteristic information of a plurality of stripes thereby acquiring a characteristic distribution in the object, and wherein
   the display control unit determines the scanning width of the receiver in the first direction based on the number of times characteristic information at the same position in the object in the characteristic distribution of each stripe is combined.

4. The object information acquisition apparatus according to claim 1, wherein the display control unit updates the guide information in accordance with a change in the specified region.

5. The object information acquisition apparatus according to claim 1, wherein the display control unit causes the display unit to display a line indicating a movement width of the receiver in the first direction based on the guide information, as the guide, and
   wherein the display control unit causes the display unit to display the line and the specified region so that the line is superimposed on the specified region.

6. The object information acquisition apparatus according to claim 5, further comprising an image capturing unit configured to capture an image of the object,
   wherein the display control unit further causes the display unit to display the line, the specified region, and the captured image of the object so that the line, the specified region, and the captured image are superimposed.

7. The object information acquisition apparatus according to claim 1, wherein in a state in which it is allowed to define the specified region, the display control unit further causes the display unit to display the specified region.

8. The object information acquisition apparatus according to claim 7, further comprising an image capturing unit configured to capture an image of the object, wherein
   in a state in which it is allowed to define the specified region, the display control unit further causes the display unit to display the captured image of the object and the specified region so that the specified region is superimposed on the captured image of the object.

9. The object information acquisition apparatus according to claim 1, wherein:
   the moving control unit moves the receiver a first movement distance of the receiver in the first direction that is shorter than a second movement distance of the receiver in the second direction.

10. The object information acquisition apparatus according to claim 1, wherein:
    the moving control unit moves the receiver a first movement distance of the receiver in the first direction that is longer than a second movement distance of the receiver in the second direction.

11. The object information acquisition apparatus according to claim 1,
    wherein the display control unit causes the display unit to display a text indicating a number of times the receiver is moved in the first direction for acquiring the characteristic information on the object in the specified region based on the guide information, as the guide.

12. An object information acquisition system comprising:
the object information acquisition apparatus according to claim 1;
the display unit configured to display the guide; and
a region specifying unit for use by a user to define the specified region.

13. A display method comprising:
displaying a captured image of an object;
displaying a specified region so that the specified region is superimposed on the captured image of the object;
displaying a guide indicating a number of times a receiver is moved in a first direction for acquiring characteristic information on the object in the specified region; and
displaying an image in terms of the characteristic information on the object in the specified region.

14. The display method according to claim 13, wherein the guide is updated in accordance with a change in the specified region.

15. The display method according to claim 13, wherein, in the step of displaying the guide, a line indicating a movement width of the receiver in the first direction as the guide is displayed so that the line is superimposed on the specified region.

16. The display method according to claim 15, wherein the line, the specified region, and the capture image of the object are displayed so that the line, the specified region, and the capture image of the object are superimposed.

17. A non-transitory storage medium in which a program is stored, the program configured to control a computer to execute processing steps comprising:
displaying a captured image of an object;
displaying a specified region so that the specified region is superimposed on the captured image of the object;
displaying a guide in terms of a number of times a receiver is moved in a first direction for acquiring characteristic information on the object in the specified region; and
displaying an image in terms of the characteristic information on the object in the specified region.

* * * * *